United States Patent
Blondel et al.

(10) Patent No.: US 10,406,498 B2
(45) Date of Patent: Sep. 10, 2019

(54) USE OF AN AMPHOLYTE COPOLYMER AS COLLOIDAL STABILIZER

(71) Applicant: S.P.C.M. SA, Andrezieux Boutheon (FR)

(72) Inventors: Frédéric Blondel, Andrezieux (FR); Guillaume Jeanson, Andrezieux (FR); Ian Harrison, Poissy (FR); Emmanuel Aussant, Paris (FR)

(73) Assignee: S.P.C.M. SA, Andrezieux Boutheon (FR)

( * ) Notice: Subject to any disclaimer, the term of this patent is extended or adjusted under 35 U.S.C. 154(b) by 101 days.

(21) Appl. No.: 15/737,601

(22) PCT Filed: Jun. 22, 2016

(86) PCT No.: PCT/EP2016/064353
§ 371 (c)(1),
(2) Date: Dec. 18, 2017

(87) PCT Pub. No.: WO2016/207187
PCT Pub. Date: Dec. 29, 2016

(65) Prior Publication Data
US 2018/0193812 A1    Jul. 12, 2018

(30) Foreign Application Priority Data

Jun. 22, 2015 (EP) ..................... 15305960

(51) Int. Cl.
| | | |
|---|---|---|
| *B01J 13/10* | (2006.01) | |
| *C11D 3/37* | (2006.01) | |
| *C11D 3/50* | (2006.01) | |
| *C11D 17/00* | (2006.01) | |
| *A61Q 13/00* | (2006.01) | |
| *A61K 8/81* | (2006.01) | |
| *A61K 8/11* | (2006.01) | |
| *C08F 220/06* | (2006.01) | |
| *C08F 220/56* | (2006.01) | |
| *C08F 220/60* | (2006.01) | |

(52) U.S. Cl.
CPC .............. *B01J 13/10* (2013.01); *A61K 8/11* (2013.01); *A61K 8/8152* (2013.01); *A61K 8/8158* (2013.01); *A61Q 13/00* (2013.01); *C08F 220/06* (2013.01); *C08F 220/56* (2013.01); *C08F 220/60* (2013.01); *C11D 3/3796* (2013.01); *C11D 3/505* (2013.01); *C11D 17/0039* (2013.01); *A61K 2800/5428* (2013.01); *C08F 2800/10* (2013.01)

(58) Field of Classification Search
CPC ...... A61K 8/11; A61K 8/8152; A61K 8/8158; A61K 2800/5428; A61Q 13/00; B01J 13/10; C08F 220/06; C08F 220/56; C08F 220/60; C08F 2800/10; C11D 17/0039; C11D 3/3796; C11D 3/505
See application file for complete search history.

(56) References Cited

U.S. PATENT DOCUMENTS

| | | |
|---|---|---|
| 2004/0071742 A1 | 4/2004 | Popplewell et al. |
| 2007/0138672 A1 | 6/2007 | Lee et al. |
| 2008/0317795 A1 | 12/2008 | Traynor et al. |
| 2010/0009893 A1 | 1/2010 | Cavin et al. |
| 2016/0166480 A1* | 6/2016 | Lei .................... C11D 17/0039 424/401 |

FOREIGN PATENT DOCUMENTS

| | | |
|---|---|---|
| EP | 1797947 A2 | 6/2007 |
| EP | 2865423 A2 | 4/2015 |

OTHER PUBLICATIONS

International Search Report and Written Opinion issued in PCT/EP2016/064353, dated Aug. 30, 2016.

* cited by examiner

Primary Examiner — Irina S Zemel
(74) Attorney, Agent, or Firm — Heslin Rothenberg Farley & Mesiti P.C.

(57) ABSTRACT

The invention relates to the use of an ampholyte copolymer as a colloidal stabilizer in the preparation of aminoplast core-shell microcapsules containing an active material, wherein the ampholyte copolymer comprises:
  2 to 99 mol % of cationic monomer having at least one quaternary ammonium group,
  1 to 98 mol % of acrylic based monomer,
  0 to 97 mol % of non-ionic monomer,
and wherein the ampholyte copolymer has more cationic charges than anionic charges, wherein the cationic charges of the ampholyte copolymer are exclusively due to the at least one quaternary ammonium group of the cationic monomer.

20 Claims, No Drawings

USE OF AN AMPHOLYTE COPOLYMER AS COLLOIDAL STABILIZER

CROSS REFERENCE TO RELATED APPLICATIONS

This application is a national stage filing under section 371 of International Application No. PCT/EP2016/064353, filed on Jun. 22, 2016, and published on Dec. 29, 2016 as WO 2016/207187, which claims priority to European Application No. 15305960.5, filed on Jun. 22, 2015. The entire contents of each of said applications are hereby incorporated herein by reference.

FIELD OF THE INVENTION

The present invention relates to the use of ampholyte copolymer as colloidal stabilizer in the preparation of aminoplast core-shell microcapsule.

BACKGROUND OF THE INVENTION

Microencapsulation technology allows to encapsulate a compound inside a tiny sphere, known as a microsphere or a microcapsule, having an average diameter as small as 1 millimeters to several micrometers. Many different active materials like drugs, enzymes, vitamins, pesticides, flavours and catalysts have been successfully encapsulated inside microcapsules made from a variety of polymeric and non-polymeric materials including poly(ethylene glycol)s, poly(methacrylate)s, poly(styrene)s, cellulose, poly(lactide)s, poly(lactide-co-glycolide)s, gelatin and acacia, etc. These microcapsules release their contents (active material) when needed thanks to different release mechanisms, which depend on the end use of the encapsulated products. This technology has been used in several fields including pharmaceutical, agriculture, food, printing, cosmetic and textile.

In particular, aminoplast core/shell microcapsules are suitable for the encapsulation of active materials for the cosmetic, textile, and agrochemicals applications.

Aminoplast microcapsules represent a widely used and industrially relevant approach in the field of microencapsulation. There are established processes of forming aminoplast microcapsules that are well documented in the prior art. Typically, in a first step, an oil-in-water emulsion is formed. This emulsion consists of active material-containing oil droplets dispersed in an aqueous continuous phase. Thereafter, shell-forming monomers or pre-condensates contained in the emulsion allow the formation of an encapsulating polymeric shell around the active material-containing droplets and therefore lead to the formation of core-shell microcapsules.

Reagents and reaction conditions are selected to ensure efficient migration of the monomers or pre-condensates to the oil-water interface so that the polymeric shells can form rapidly around the oil droplets, thereby retaining all, or substantially all, of the active material within the cores and preventing leakage of encapsulated active material from the microcapsule cores. If the shell-forming materials do not migrate to the oil-water interface quickly or in sufficient amounts, it may be impossible to form microcapsules. In that case, if microcapsules are formed, they may be characterized by poor active material retention and may be prone to agglomeration.

Polymers, acting as protective colloids stabilizer, are employed to stabilize the oil-water interface during the microcapsule formation. The polymeric stabilizer functions in several ways: it ensures that stable oil-in-water emulsions are formed; it facilitates migration of monomers and pre-condensates to the oil-water interface; and it provides a template around which the monomers or pre-condensates can react to form the encapsulating polymeric shells.

Polymeric stabilizers employed in the preparation of aminoplast microcapsules are anionic or non-ionic polymers, see for example U.S. Pat. No. 8,119,587. Particularly effective polymeric stabilizers are acrylic acid-based copolymers bearing sulphonate groups. Examples of commercially available copolymers include LUPASOL® (ex BASF), such as LUPASOL PA 140, or LUPASOL VFR. These commercial polymers are exemplary polymeric stabilizers, which are employed in the preparation of commercial aminoplast microcapsule compositions.

The aminoplast microcapsules prepared by the process described above are typically collected in the form of a slurry comprising a plurality of microcapsules suspended in a suitable suspending medium. The microcapsule slurry may then be used directly in applications, or further processed. For example, it is conventional to post-coat aminoplast microcapsules with a cationic water-soluble polymer in order to provide them with a net positive charge. This coating acts as a deposition aid and increases the substantivity of the microcapsules when deposited on certain substrates. However, post-coating requires an extra step, which increases the cost of the manufacturing process. Indeed, large amounts of cationic polymer are necessary to first neutralize the negatively charged microcapsules before these microparticles can finally have a net positive charge.

As a result, there is a need to develop microcapsules with an increase of stability and a better control of the thickness. Moreover there is a need to improve the preparation of microcapsules without using conventional post-coating techniques.

SUMMARY OF THE INVENTION

The invention relates to using an ampholyte copolymer as colloidal stabilizer in a method for the preparation of core-shell microcapsules in which the core comprises an active material. This ampholyte copolymer improves:
- the stability of the emulsion in which the microcapsules are formed;
- the control of the thickness of the microcapsules' shell;
- the prevention of the formation of agglomerates of microparticles;
- the stability of an aqueous composition, or slurry, comprising the microcapsules.

Herein and thereafter, the term "microcapsule(s)" refers to "aminoplast core-shell microcapsule(s)".

An ampholyte copolymer, in accordance with the present invention is defined herein below. It contains both cationic and anionic charges. Its cationic charges are pH independent. In other words, regardless of the solution in which the polymer may be solubilized or suspended, its cationic charge density remains the same.

Accordingly, the present invention relates to the use of an ampholyte copolymer as a colloidal stabilizer in the preparation of aminoplast core-shell microcapsules containing an active material, wherein the ampholyte copolymer comprises:
- 2 to 99 mol % of cationic monomer having at least one quaternary ammonium group, preferably one quaternary ammonium group;
- 1 to 98 mol % of acrylic based monomer;
- 0 to 97 mol % of non-ionic monomer;

and wherein the ampholyte copolymer has more cationic charges than anionic charges.

The ratio of cationic and anionic functionalities therefore results in a net total charge of positive.

The cationic charges of the ampholyte copolymer are exclusively due to the quaternary ammonium group(s) of the cationic monomer.

The presence of a non-ionic monomer is optional.

Here and thereafter, the total mole percentage of monomers is 100. The skilled man in the art will be able to adjust the respective mole percentages of the cationic monomer, acrylic based monomer (anionic) and non-ionic monomer so as to reach 100.

As explained before, typical aminoplast core-shell microcapsules are prepared as follows:
   In a first step, an oil-in-water emulsion is formed, consisting of active-containing oil droplets dispersed in an aqueous continuous phase.
   Shell-forming precursors (monomers or pre-condensates) contained in the emulsion are caused to form encapsulating polymeric shells around the active material-containing droplets so as to form core-shell microcapsules.

According to a particular embodiment, the ampholyte copolymer may be used as colloidal stabilizer in a method for preparing aminoplast core-shell microcapsules according to the following steps:
   preparation of an aqueous phase comprising the ampholyte copolymer and aminoplast resin precursor(s);
   addition of an active material, preferably a hydrophobic active material, to this aqueous phase;
   coacervation or emulsification of the resulting composition;
   formation of aminoplast core-shell microcapsules by polymerization or crosslinking of the aminoplast resin precursor(s).

The resulting microcapsules are preferably suspended in the aqueous phase. The resulting suspension may be used without any purification step, or eventually dried. The aqueous phase generally comprises at least some of the ampholyte copolymer.

The aminoplast resin precursor(s) may be a mixture of pre-condensate and crosslinker or a mixture of monomers.

According to another particular embodiment, once the core-shell microcapsules are formed, a cationic copolymer may be added to the resulting composition, so as to improve the stability of the aqueous composition, or slurry, comprising the microcapsules.

The aminoplast core-shell microcapsules prepared by the process described above are typically collected in the form of a slurry comprising a plurality of microcapsules suspended in a suitable suspending medium.

As already mentioned, the ampholyte copolymer of the invention comprises at least one cationic monomer, at least one acrylic based monomer and optionally at least one non-ionic monomer.

The cationic monomer(s) may be chosen, in particular, from monomers such as derivatives of the following monomers having a quaternary ammonium group: acrylamide, acrylic, vinyl, allyl or maleic. In particular and in a non-limiting way, the cationic monomer is preferably selected from the group consisting of quaternized dimethylaminoethyl acrylate (ADAME), quaternized dimethylaminoethyl methacrylate (MADAME), dimethyldiallyl ammonium chloride (DADMAC), acrylamidopropyltrimethylammonium chloride (APTAC) and methacrylamidopropyltrimethylammonium chloride (MAPTAC). The cationic monomer may also be a mixture of cationic monomers. The most preferred cationic monomer is MAPTAC.

The cationic monomer represents 2 to 99 mole %, preferably 30 to 95 mole %, more preferably 60 to 90 mole %, as compared to the total number of moles of monomers of the ampholyte copolymer.

The acrylic based monomers may be selected from monomers having acrylic, vinyl, maleic, fumaric or allyl functionalities and having a carboxy, phosphonate, sulfonate or other group with an anionic charge. It may also be the ammonium salt or alkaline-earth metal salt or alkaline metal salt of such monomers.

Examples of suitable acrylic based monomers include acrylic acid, methacrylic acid, itaconic acid, crotonic acid, maleic acid, fumaric acid and strong-acid monomers, for example monomers with a sulfonic or a phosphonic acid-type function such as 2-acrylamido-2-methylpropane sulfonic acid, vinylsulfonic acid, vinylphosphonic acid, allylsulfonic acid, allylphosphonic acid, styrene sulfonic acid. The acrylic based monomer may also be any water-soluble salts of these monomers; wherein the salt is a salt of an alkali metal, an alkaline-earth metal or an ammonium. It may also be a mixture of acrylic based monomers. The most preferred acrylic based monomer is acrylic acid, methacrylic acid, or a water soluble salt thereof.

The acrylic based monomer represents 1 to 98 mole %, preferably 5 to 70 mole %, more preferably 10 to 40 mole %, as compared to the total number of moles of monomers of the ampholyte copolymer.

Optionally, the ampholyte copolymer comprises at least one non-ionic monomer. The useful non-ionic monomer in this invention can be selected from the group including water-soluble vinyl monomers. The preferred non-ionic monomer belonging to this category is advantageously selected from the group consisting of acrylamide, methacrylamide, N-isopropylacrylamide, NN-dimethylacrylamide, N-methylolacrylamide. N-vinylformamide, N-vinyl acetamide, N-vinylpyridine and/or N-vinylpyrrolidone can also be used. It may also be a mixture of non-ionic monomers. The most preferred non-ionic monomer is acrylamide.

The non-ionic monomer represents 0 to 97 mole %, preferably 0 to 80 mole %, more preferably 0 to 50 mole %, as compared to the total number of moles of monomers of the ampholyte copolymer.

The ampholyte copolymer contains cationic and acrylic based monomers and optionally non-ionic monomers. The ampholyte copolymer has a ratio of cationic and anionic functionalities resulting in a net total charge of positive. In other words, the ampholyte copolymer has a greater number of positive functions that generally result from the cationic monomer as compared to the number of negative functions that generally result from the acrylic based monomer. The molar percentage of cationic monomer is preferably greater than the molar percentage of acrylic based monomer.

According to a preferred embodiment, the ampholyte copolymer comprises:
   30 to 95 mol % of methacrylamidopropyltrimethylammonium chloride (MAPTAC), preferably 60 to 90 mol %;
   5 to 70 mol % of acrylic acid or a water soluble salt thereof, preferably 10 to 40 mol %;
   0 to 80 mol % of acrylamide, preferably 0 to 50 mol %.
   Preferably, the ampholyte copolymer has a molecular weight of at least 100,000 g/mol, and more preferably of at least 500,000 g/mol.

The amount of polymeric stabilizer (ampholyte copolymer) that may be employed in a method for preparing a microcapsule according to the present invention may range from 0.001% to 20%, preferably 0.01 to 10%, more preferably 0.01 to 5% by weight based on the weight of the composition allowing the formation of the microparticles for instance the above mentioned oil-in-water emulsion.

The amount of polymeric stabilizer (ampholyte copolymer) that may be employed in a microcapsule composition (preferably a slurry) according to the present invention may range from 1% to 20%, more preferably 2 to 10% by weight based on the weight of the composition.

In general, the ampholyte copolymer of the invention does not require the development of any specific polymerization process. Indeed, it may be obtained according to all the polymerization techniques well known to a person skilled in the art. These known polymerization techniques include solution polymerization; gel polymerization; precipitation polymerization; inverse emulsion polymerization; aqueous emulsion polymerization; suspension polymerization; and micellar polymerization.

According to the invention, and in an advantageous manner, the ampholyte copolymer is not crosslinked. It may be linear or structured. A structured copolymer may be branched, star-shaped (in the form of a star) or comb-shaped (in the form of a comb). These structures may be obtained by free selection of the initiator, the transfer agents, the polymerization technique such as controlled radical polymerization, the incorporation of structural monomers, the concentration, etc. Suitable structural monomers include polyvalent metal salts, formaldehyde, glyoxal, or also, and preferably, covalent crosslinking agents capable of copolymerizing with the monomers and preferably monomers having polyethylenic unsaturation (having a minimum of two unsaturated functional groups), such as, for example, methylene bisacrylamide (MBA), triallyamine, polyethylene glycol diacrylate. Alternatively, macro initiators such as polyperoxides, polyazo compounds and polytransfer agents such as polymercaptan polymers may be used.

According to the invention, the ampholyte copolymer can be present in aqueous continuous phase of the emulsion before the formation of the microcapsule. More preferably the ampholyte copolymer is present in aqueous continuous phase of the emulsion before the formation of the microcapsule. The ampholyte copolymer is preferably present in the aqueous phase before formation of the emulsion. It may be added during the formation of the emulsion.

According to the invention, the active material is present in the oil droplets before the formation of the microcapsule. Preferably, the active material is hydrophobic. A hydrophobic active material refers to any of the following field: personal care, fabric care, surface care, or agriculture material. The hydrophobic active material has a solubility in water of less than 100 ppm, more preferably of less than 10 ppm. Personal care hydrophobic active materials include emollients, moisturizers, fragrances, vitamins, anti-aging active materials, and sunscreens typically used in personal care compositions in amounts of which falls within the regulatory approved limits. In a preferred embodiment, the personal care agent is a sunscreen agent. Examples of sunscreen agents include, but are not limited to, p-aminobenzoic acid as well as salts and esters thereof; o-aminobenzoic acid and o-aminobenzoates (including methyl, menthyl, phenyl, benzyl, phenylethyl, linalyl, terpinyl, and cyclohexenyl esters thereof); salicylic acid and salicylates (including octyl, amyl, phenyl, benzyl, menthyl, glyceryl, and dipropyleneglycol esters thereof); cinnamic acid and derivatives thereof (including methyl and benzyl esters, alkyl alkoxycinnamates such as octyl methoxycinnamate also known as 2-ethylhexyl-4-methoxycinnamate, alpha-phenyl cinnamonitrile, and butyl cinnamoyl pyruvate); dihydroxycinnamic acid and its derivatives; trihydroxycinnamic acid and its derivatives; diphenylbutadiene and stilbene; dibenzalacetone and benzalacetophenone; I naphthosulfonates (such as sodium salts of 2-naphthol-3,6-disulfonic acid and 2-naphthnol 6,8-disulfonic acid); dihydroxynaphthoic acid and its salts; o- and p-hydroxydiphenyldisulfonates; coumarin and derivatives thereof (such as 7-hydroxy, 7-methyl, and 3-phenyl coumarin); diazoles; quinine salts; quinoline and derivatives thereof; hydroxybenzophenones; alkoxybenzophenones; uric and vilouric acids; tannic acid and derivatives thereof; hydroquinone; benzophenones (such as oxybenzone, sulisobenzone, dioxybenzone, benzoresorcinol,2,2',4,4'-tetrahydroxybenzophenone, 2,2'-dihydroxy-4, 4'-dimethoxybenzophenone, octabenzone, 4-isopropyldibenzoylmethane,-4-butylmethoxydibenzoylmethane, etocrylene, and 4-isopropyl-dibenzoylmethane), and mixtures thereof. In some embodiments, the sunscreen agents include ethylhexyl salicylate, homosalate, butyl methoxydibenzoylmethane, octocrylene, phenylbenzimidazole sulfonic acid, benzophenone-3, benzophenone-4, benzophenone-5, n-hexyl 2-(4-diethylamino-2-hydroxybenzoyl) benzoate, 4-methylbenzylidene camphor, terephthalylidene dicamphor sulfonic acid, disodium phenyl dibenzimidazole tetrasulfonate, methylene bis-benzotriazolyl tetramethylbutylphenol, bis-ethylhexyloxyphenol methoxyphenyl triazine, ethylhexyl triazone, diethylhexyl butamido triazone, 2,4,6-tris(dineopentyl 4'-aminobenzalmalonate)-s-triazine, 2,4,6-tris (diisobutyl 4'-aminobenzalmalonate)-s-triazine, 2,4-bis(n-butyl 4'-aminobenzoate)-6-(aminopropyltrisiloxane)-s-triazine, 2,4-bis(dineopentyl 4'-aminobenzalmalonate)-6-(n-butyl 4'-aminobenzoate)-s-triazine, 2,4,6-tris(biphenyl-4-yl)-1,3, 5-triazine, 2,4,6-tris(terphenyl)-1,3,5-triazine, drometrizole trisiloxane, poly silicone-15, 1,1-dicarboxy (2, 2'-dimethylpropyl)-4,4-diphenylbutadiene, 2,4-bis [5-1-(diraethylpropyl) benzoxazol-2-yl (4-phenyl) imino]-6-(2-ethylhexyl)-imino-1,3,5-triazine, and any mixtures thereof. In one embodiment, the sunscreen agent is paraminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide and zinc oxide, diethanolamine methoxycinnamate, digalloy trioleate, ethyl dihydroxypropyl PABA (4-[bis(2-hydroxypropyl)amino]benzoic acid ethyl ester), glycerylaminobenzoate, lawsone with dihydroxy acetone, red petrolatum, and any combinations thereof. In one preferred embodiment, the sunscreen agent is octyl methoxycinnamate, in another preferred embodiment the sunscreen agent is avobenzone (1-(4-methoxyphenyl)-3-(4-tert-butylphenyl) propane-1,3-dione).

Other active materials include triclosan, polyphenols, flavonoids and isoflavonoids, coenzyme Q10 (CoQlO) and derivatives thereof, carotene and derivatives thereof, salicylic acid and derivatives thereof, dehydroepiandrosterone (DHEA), hydrophobic polysaccharides, proteins, including enzymes and peptides, and botanicals. Exemplary vitamins include Vitamin A and esters thereof, Vitamin D and derivatives thereof, Vitamins B3 and B5 and derivatives thereof, Vitamin E and esters thereof, Vitamin F and derivatives thereof, and Vitamin K.

In one embodiment, the hydrophobic active material is a fragrance oil. Examples include scents that are floral, ambery, woody, leather, chypre, fougere, musk, mint, vanilla, fruit, and/or citrus. Fragrance oils are obtained by extraction of natural substances or synthetically produced. In one embodiment, the fragrance oil is one or more of an essential oil.

The term "agricultural active material" as used herein refers to an active material used in agriculture, horticulture and pest management for protection of crops, plants, structures, humans and animals against unwanted organisms such as fungal and bacterial plant pathogens, weeds, insects, mites, algae, nematodes and the like. Specifically, active materials used for these purposes include fungicides, bactericides, herbicides, insecticides, miticides, algaecides, nemtocides and fumigants. The term "agricultural active material" also includes insect attractants, repellants and pheromones, modifiers of plant physiology or structure, and herbicide safeners.

Without putting forward any theory, at the end of the formation of microcapsule, the ampholyte copolymer seems embedded in the shell, and unlike the prior art post-coating method, the copolymer cannot be washed out. As a result, the charge on the microcapsules is stable, or substantially stable, over time and insensitive, or substantially insensitive, to the conditions of the external suspending medium.

Although it was entirely surprising that a positively charged ampholyte copolymer could act as a colloidal stabilizer, it also considerably simplify the manufacturing process. Furthermore, it enables a precise control of the microcapsule shell thickness, of the shell quality. It also enables to predict the release rates of active materials.

Aminoplast resins used in the present invention may be formed of any of the amino aldehyde resins known in the art. The amino aldehyde resin may be a polymer or copolymer of:
  at least one amine, such as urea, thiourea, alkyl urea, 6-substituted-2,4-diamino-1,3,5-triazines such as benzoguanamine, glycoluril, or melamine; and
  at least one aldehyde, such as formaldehyde, acetaldehyde, glyoxal or glutaraldehyde.

The aminoaldehyde resin may be formed either by polycondensation of the above-mentioned monomers, or by first preparing water-soluble amino aldehyde pre-polymers of the above monomers and performing a poly-condensation reaction with said pre-polymers. A further alternative is to carry out a poly-condensation reaction on both monomers and pre-polymers (also called pre-condensates).

In a preferred embodiment, melamine-formaldehyde pre-polymers are used in the formation of aminoplast core-shell microcapsules. Melamine-formaldehyde pre-polymers are formed by the reaction of melamine with formaldehyde to form methylolated melamine. Methylolated melamine may also be treated with methanol to form methoxymethylated methylol melamine.

Encapsulated compositions of the present invention may be comprised of microcapsules having a volume average diameter (D 50) anywhere between 1 and 1000 µm, if desired. However, stable and performing encapsulated active material compositions more typically comprise microcapsules that have an average diameter (D 50) between 5 µm to 50 µm, still more particularly 5 µm to 20 µm, for example 10 µm. The volume average diameter may be obtained by conducting light scattering measurements, using techniques generally known in the art. For instance a Malvern 2000S instrument may be used.

The invention and its advantages will become more apparent to one skilled in the art from the following examples.

EXAMPLES

Preparation of an Ampholyte Polymer [AP] According to the Invention

The polymer of the invention is obtained using the following protocol. The example is carried out with an acrylic acid/MAPTAC copolymer. In order to produce this polymer, the following compounds are introduced in the reactor:
  464 g of MAPTAC (50% in water)
  34.4 g of Acrylic acid (90% in water)
  119 g of water
  0.03 g of EDTA
  0.14 g of sodium hypophosphite
  The pH of the reaction medium is adjusted at 5.0-5.2, by using NaOH.
  53 g of 2,2'-azobis (2-amidinopropane) di-hydrochloride (10% in water) are also introduced in the reactor.

The reaction medium is maintained at 85° C. during 1 hour. Then 1.3 g of sodium bisulfite solution (40% in water) is added in one shot in the reactor. After 1 hour of aging, the product is diluted by adding 255 g of water.

Example 1

Preparation of an Encapsulated Perfume Composition According to the Invention

One kilogram of encapsulated perfume composition slurry is formed according to the following method:

A reactor set to a temperature of 20° C. is charged with deionised water (550 g); resorcinol as cross-linker (10 g); polymer [AP] (2 g); and melamine formaldehyde precondensate (Luracoll SD) (5 g). The stirring speed is set to 400 rpm (rounds per minute). At this stage, a perfume composition (300 g) is added.

Coacervation is undertaken in the following manner: Formic acid (10%) is added and the mixture is stirred for 1 hour at 35° C. Then, the reactor temperature is increased to 90° C. for 1 hour.

Finally, the mixture is cooled. After stirring the cooled mixture for one hour, caprylyl glycol (4 g) and phenoxy ethanol (4 g) are added. A cationic suspending agent (Flosoft FS222) is added to the mixture over a 30 minute period under stirring. Finally, the pH of the slurry is adjusted to a pH range of 5.7 to 6.7 by adding ammonia (1 g). Thereafter, the slurry of encapsulated perfume composition is discharged from the reactor.

Example 2

Preparation of a Comparative Encapsulated Perfume Composition Using an Anionic Polymeric Stabilizer (Lupasol PA 140)

One kilogram of encapsulated perfume composition slurry is formed according to the following method:

A reactor set to a temperature of 20° C. is charged with deionised water (550 g); resorcinol as cross-linker (10 g); polymeric stabilizer Lupasol PA 140 (10 g); and melamine formaldehyde precondensate (Luracoll SD) (5 g). The stirring speed is set to 400 rpm At this stage, a perfume composition (300 g) is added.

Coacervation is undertaken in the following manner: Formic acid (10%) is added and the mixture is stirred for 1 hour. Then the reactor temperature is increased to 90° C. for 1 hour. Finally, the mixture is cooled. After stirring the cooled mixture for one hour, caprylyl glycol (4 g) and phenoxy ethanol (4 g) are added. Finally, the pH of the slurry is adjusted to a pH range of 5.7 to 6.7 by adding ammonia (1 g). Thereafter, the slurry of encapsulated perfume composition is discharged from the reactor.

In the form of a slurry, the encapsulated perfume composition of Example 1 has a particle size distribution (D 50) of 8 microns, whereas that of Example 2 has a D 50 of 11 microns. However, when the respective compositions are incorporated into a fabric softener base, the comparative composition of Example 2 forms agglomerates (D 50=100), whereas the D 50 of the inventive composition appears to be substantially unchanged (D50=11), indicating no agglomeration.

Example 2b

Preparation of a Comparative Encapsulated Perfume Composition Using the Ampholytic Copolymer, Prepared in Accordance with the Method Described Example 1 Above, Wherein the Copolymer is Added During Crosslinking A reactor set to a temperature of 20° C. and is charged with deionised water (550 g); resorcinol as cross-linker (10 g); and melamine formaldehyde precondensate (Luracoll SD) (5 g). The stirring speed is set to 400 rpm. At this stage, a perfume composition (300 g) is added.

Coacervation is undertaken in the following manner: Formic acid (10%) is added and the mixture is stirred for 1 hour at 35° C. The reactor temperature is then increased to 90° C. and held at that temperature for 1 hour to affect cross-linking. During the increase in temperature, when the reactor temperature reaches 60° C., the positively charged ampholytic copolymer [AP] (2 g) is added to the mixture.

Finally, the mixture is cooled. After stirring the cooled mixture for one hour, caprylyl glycol (4 g) and phenoxy ethanol (4 g) are added. A cationic suspending agent (Flosoft FS222) is added to the mixture over a 30 minute period under stirring. Finally, the pH of the slurry is adjusted to a pH range of 5.7 to 6.7 by adding a quantity of Ammonia (1 g). Thereafter, the slurry of encapsulated perfume composition is discharged from the reactor.

The slurry obtained was of poor quality. D50 measurements indicated a wide particle size distribution indicating the formation of aggregates, many of which were actually visible.

The invention claimed is:

1. A method of preparing aminoplast core-shell microcapsules containing an active material, the method comprising using an ampholyte copolymer as a colloidal stabilizer, wherein the ampholyte copolymer comprises:
   2 to 99 mol % of cationic monomer having at least one quaternary ammonium group,
   1 to 98 mol % of acrylic based monomer,
   0 to 97 mol % of non-ionic monomer,
and wherein the ampholyte copolymer has more cationic charges than anionic charges, wherein the cationic charges of the ampholyte copolymer are exclusively due to the at least one quaternary ammonium group of the cationic monomer.

2. The method according to claim 1, wherein the cationic monomer is chosen from the group consisting of quaternized dimethylaminoethyl acrylate (ADAME), quaternized dimethylaminoethyl methacrylate (MADAME), dimethyldiallylammonium chloride (DADMAC), acrylamidopropyltrimethylammonium chloride (APTAC) and methacrylamidopropyltrimethylammonium chloride (MAPTAC).

3. The method according to claim 1, wherein the cationic monomer is methacrylamidopropyltrimethylammonium chloride (MAPTAC).

4. The method according to claim 1, wherein the acrylic based monomer is chosen from the group consisting of acrylic acid, methacrylic acid, itaconic acid, crotonic acid, maleic acid, fumaric acid, 2-acrylamido-2-methylpropane sulfonic acid, vinylsulfonic acid, vinylphosphonic acid, allylsulfonic acid, allylphosphonic acid, styrene sulfonic acid, and their water-soluble salts of an alkali metal, alkaline-earth metal or ammonium.

5. The method according to claim 1, wherein the acrylic based monomer is (meth)acrylic acid or a water soluble salt thereof.

6. The method according to claim 1, wherein the non-ionic monomer is chosen from the group consisting of acrylamide, methacrylamide, N-isopropylacrylamide, N N-dimethylacrylamide, N-methylolacrylamide, N-vinylformamide, N-vinyl acetamide, N-vinylpyridine and N-vinylpyrrolidone.

7. The method according to claim 1, wherein the non-ionic monomer is acrylamide.

8. The method according to claim 1, wherein the ampholyte copolymer comprises 30 to 95 mol % of cationic monomer.

9. The method according to claim 1, wherein the ampholyte copolymer comprises 60 to 90 mol % of cationic monomer.

10. The method according to claim 1, wherein the ampholyte copolymer comprises 5 to 70 mol % of acrylic based monomer.

11. The method according to claim 1, wherein the ampholyte copolymer comprises 10 to 40 mol % of acrylic based monomer.

12. The method according to claim 1, wherein the ampholyte copolymer comprises:
   30 to 95 mol % of methacrylamidopropyltrimethylammonium chloride (MAPTAC) %;
   5 to 70 mol % of acrylic acid or a water soluble salt thereof; and
   0 to 80 mol % of acrylamide.

13. The method according to claim 1, wherein the ampholyte copolymer has a molecular weight of at least 100,000 g/mol.

14. The method according to claim 1, wherein the ampholyte copolymer has a molecular weight of at least 500,000 g/mol.

15. The method according to claim 1, wherein the ampholyte copolymer is linear, branched, star-shaped, or comb-shaped.

16. The method according to claim 2, wherein the acrylic based monomer is chosen from the group consisting of acrylic acid, methacrylic acid, itaconic acid, crotonic acid, maleic acid, fumaric acid, 2-acrylamido-2-methylpropane sulfonic acid, vinyl sulfonic acid, vinylphosphonic acid, allylsulfonic acid, allylphosphonic acid, styrene sulfonic acid, and their water-soluble salts of an alkali metal, alkaline-earth metal or ammonium.

17. The method according to claim 2, wherein the acrylic based monomer is (meth)acrylic acid or a water soluble salt thereof.

18. The method according to claim 2, wherein the non-ionic monomer is chosen from the group consisting of acrylamide, methacrylamide, N-isopropylacrylamide, N N-dimethylacrylamide, N-methylolacrylamide, N-vinylformamide, N-vinyl acetamide, N-vinylpyridine and N-vinylpyrrolidone.

19. The method according to claim 16, wherein the non-ionic monomer is chosen from the group consisting of acrylamide, methacrylamide, N-isopropylacrylamide, N N-dimethylacrylamide, N-methylolacrylamide, N-vinylformamide, N-vinyl acetamide, N-vinylpyridine and N-vinylpyrrolidone.

20. The method according claim 1, wherein the ampholyte copolymer comprises:
- 60 to 90 mol % of methacrylamidopropyltrimethylammonium chloride (MAPTAC);
- 10 to 40 mol % of acrylic acid or a water soluble salt thereof; and
- 0 to 50 mol % of acrylamide.

\* \* \* \* \*